US009888329B2

(12) United States Patent
Andersson

(10) Patent No.: US 9,888,329 B2
(45) Date of Patent: *Feb. 6, 2018

(54) IMPLANT ABUTMENT

(71) Applicant: Cochlear Limited, Macquarie University, NSW (AU)

(72) Inventor: Marcus Andersson, Gothenburg (SE)

(73) Assignee: Cochlear Limited, Macquarie University, NSW (AU)

( * ) Notice: Subject to any disclaimer, the term of this patent is extended or adjusted under 35 U.S.C. 154(b) by 71 days.

This patent is subject to a terminal disclaimer.

(21) Appl. No.: 14/685,048

(22) Filed: Apr. 13, 2015

(65) Prior Publication Data
US 2015/0215711 A1 Jul. 30, 2015

Related U.S. Application Data

(63) Continuation of application No. 12/601,801, filed as application No. PCT/SE2008/000337 on May 20, 2008, now Pat. No. 9,005,202.

(30) Foreign Application Priority Data

May 24, 2007 (SE) ...................... 0701244

(51) Int. Cl.
*A61B 17/58* (2006.01)
*H04R 25/00* (2006.01)
*A61F 2/00* (2006.01)

(52) U.S. Cl.
CPC ......... *H04R 25/606* (2013.01); *A61F 2/0077* (2013.01); *H04R 2225/67* (2013.01); *H04R 2460/13* (2013.01)

(58) Field of Classification Search
CPC .................... H04R 25/606; H04R 2225/67
See application file for complete search history.

(56) References Cited

U.S. PATENT DOCUMENTS

| 4,052,754 | A | 10/1977 | Homsy |
| 4,498,461 | A | 2/1985 | Hakansson |
| 4,612,915 | A | 9/1986 | Hough et al. |
| 4,645,504 | A | 2/1987 | Byers |
| 4,818,559 | A | 4/1989 | Hama et al. |
| 4,915,628 | A | 4/1990 | Linkow et al. |
| 5,026,397 | A | 6/1991 | Aoki et al. |
| 5,049,074 | A | 9/1991 | Otani et al. |

(Continued)

FOREIGN PATENT DOCUMENTS

| CA | 1068052 A1 | 12/1979 | |
| CA | 2485716 | * 4/2005 | ............ A61L 27/04 |

(Continued)

OTHER PUBLICATIONS

International Search Report for PCT/SE2008/000337 dated Jul. 16, 2008.

*Primary Examiner* — Christian Sevilla
(74) *Attorney, Agent, or Firm* — Hauptman Ham, LLP; Martin J. Cosenza

(57) ABSTRACT

The present invention relates to a percutaneous implant abutment for bone anchored implant devices adapted to be anchored in the craniofacial region of a person, such as bone anchored hearing aids. The abutment comprises a skin penetration body having a skin contacting surface. The skin contacting surface has been modified.

36 Claims, 2 Drawing Sheets

(56) References Cited

U.S. PATENT DOCUMENTS

| | | | |
|---|---|---|---|
| 5,456,717 | A | 10/1995 | Zweymuller et al. |
| 5,645,580 | A | 7/1997 | Moaddeb et al. |
| 5,735,790 | A | 4/1998 | Håkansson |
| 5,857,958 | A | 1/1999 | Ball et al. |
| 5,951,601 | A | 9/1999 | Lesinski et al. |
| 6,589,216 | B1 | 7/2003 | Abbott et al. |
| 6,705,985 | B2 | 3/2004 | Easter et al. |
| 7,806,693 | B2 | 10/2010 | Hurson |
| 8,469,908 | B2 | 6/2013 | Asfora |
| 2001/0047175 | A1 | 11/2001 | Doubler et al. |
| 2003/0176866 | A1 | 9/2003 | Westerkull |
| 2004/0132143 | A1 | 7/2004 | DeAngelis et al. |
| 2004/0204686 | A1 | 10/2004 | Porter et al. |
| 2004/0215164 | A1 | 10/2004 | Abbott et al. |
| 2005/0026113 | A1 | 2/2005 | Chen et al. |
| 2005/0106534 | A1 | 5/2005 | Gahlert |
| 2005/0113834 | A1 | 5/2005 | Breitenstien et al. |
| 2005/0142163 | A1 | 6/2005 | Hunter et al. |
| 2006/0050913 | A1 | 3/2006 | Westerkull |
| 2006/0093175 | A1 | 5/2006 | Westerkull |
| 2006/0241592 | A1 | 10/2006 | Myerson et al. |
| 2007/0009853 | A1 | 1/2007 | Pitulia |
| 2007/0270631 | A1 | 11/2007 | Nelson et al. |
| 2009/0082817 | A1 | 3/2009 | Jinton et al. |
| 2010/0249784 | A1 | 9/2010 | Andersson |

FOREIGN PATENT DOCUMENTS

| | | |
|---|---|---|
| EP | 0 367 354 A1 | 5/1990 |
| JP | 6-192852 A | 7/1994 |
| WO | 98/55049 A1 | 12/1998 |
| WO | 01/97718 A1 | 12/2001 |
| WO | 02/09622 A1 | 1/2002 |
| WO | 2004091432 A2 | 10/2004 |
| WO | 2005037153 A1 | 4/2005 |

\* cited by examiner

IMPLANT ABUTMENT

CROSS-REFERENCE TO RELATED APPLICATIONS

This application is a continuation application of U.S. application Ser. No. 12/601,801, filed on May 21, 2010, which is a national stage application under 35 USC § 371 (c) of PCT Application No. PCT/SE2008/000337, entitled "IMPLANT ABUTMENT," filed on May 20, 2008, which claims priority from Swedish Patent Application No. 0701244-6, filed on May 24, 2007. This application is related to commonly owned and co-pending U.S. Utility patent application entitled "VIBRATOR FOR BONE CONDUCTING HEARING DEVICES," filed Nov. 24, 2009, which is a national stage application of PCT Application No. PCT/SE2008/000336, filed May 21, 2008. This application is also related to commonly owned and co-pending U.S. Utility patent application entitled "ANCHORING ELEMENT" which is a national stage application under 35 USC § 371 (c) of PCT Application No. PCT/SE2008/000338, filed on May 21, 2008. The entire disclosure and contents of the above applications are hereby incorporated by reference herein in their entirety.

BACKGROUND

Field of the Invention

The present invention relates generally to bone anchored implant devices, and more particularly, to a percutaneous implant abutment for bone anchored implant devices adapted to be anchored in the craniofacial region of a person.

Related Art

There are a variety of medical devices that include a bone anchored implant device. An example of such medical devices is the, bone conduction hearing aid devices such as bone anchored hearing implants. An example of a bone anchored hearing implant is the Baha®, commercially available from Cochlear Bone Anchored Solutions AB in Goteborg, Sweden. The Baha® and other bone anchored implant devices comprise an external unit which transforms sound to mechanical vibrations which are conducted via the abutment and the fixture into the bone of the skull. The vibrations are transmitted mechanically via the skull bone directly to the inner ear of a person with impaired hearing and allows for the hearing organ to register the sound. A hearing aid device of the BAHA® type is connected to an anchoring element in the form of an implanted titanium screw installed in the bone behind the external ear. Sound is transmitted via the skull bone to the cochlea irrespective of a disease in the middle ear. The bone anchoring principle means that the skin is penetrated which makes the vibratory transmission very efficient.

This type of hearing aid device has been a revolution for the rehabilitation of patients with certain types of impaired hearing, but also as anti-stuttering means. It is very convenient for the patient and almost invisible with normal hair styles. It can easily be connected to the implanted titanium fixture by means of a bayonet coupling or a snap in coupling. One example of this type of hearing aid device is described in U.S. Pat. No. 4,498,461 and in SE 9702164-6 it is described a one-piece implant of this type, in which the fixture is integrated with a first coupling device. In WO 2005/037153 it is described how this type of hearing aid device can be used as an anti-stuttering device.

A well known problem with percutaneous implants is the infections and inflammation at the skin-implant interface. The infections are a result of bacterial colonization occurring at the area around the interface. There is generally a lack of integration of the skin to the implant which results in a gap between the two. This gap is unfortunately an ideal environment for the bacteria and if this zone is not properly managed, it is likely that an infection will occur. By creating an integration of the skin to the implant the adverse skin reactions associated with bone anchored percutaneous implants are expected to be reduced.

Creating integration between the skin and the implant requires that the implant is suitable for this purpose and that the soft tissue does not dissociate itself from the skin penetrating implant abutment by encapsulating the abutment in fibrous tissue.

In the field of dental implants it is previously known to use different types of abutments which penetrate the oral mucosa. However, it should be understood that there is a physiological difference between breaching the skin barrier compared to the oral mucosa. In the oral cavity the skin is not involved and there is another type of force situation. In contrast to dental implants the present invention relates to extraoral implants.

It is recognized that bone anchored percutaneously implants are subjected to mostly shear forces, while percutaneously implants which are not bone anchored are subjected to several other types of forces, such as pull and torsion. Such different types of forces are also mostly involved in dental applications. Mostly shear forces are especially the case for implants with inherent movements such as bone anchored hearing implants due to the generation of vibratory movements.

It is also recognized that the effect that the shear forces has on the skin leads to tissue damage not only from a mechanical point of view but, more importantly, an indirect biological reaction which leads to foreign body reaction or dissociation from the material (encapsulation of the implant by fibrous tissue, etc). Some reactions are acute and some are noticed after several weeks.

SUMMARY

In one aspect of the present invention, a percutaneous implant for bone anchored implant devices adapted to be anchored in the craniofacial region of a person is provided. The implant comprises: a screw-shaped bone anchoring element; an abutment, comprising: a skin penetration body having a skin contacting surface; and a biocompatible coating disposed on the skin contacting surface.

BRIEF DESCRIPTION OF THE DRAWINGS

Illustrative embodiments of the present invention will be described herein with reference to the accompanying figures, in which.

DETAILED DESCRIPTION

The present invention relates generally to bone anchored implant devices, and more particularly, to a percutaneous implant abutment for bone anchored implant devices adapted to be anchored in the craniofacial region of a person, such as bone anchored hearing aids. Implant devices of this type normally comprise a screw-shaped bone anchoring element (fixture) for permanent anchorage in the bone tissue and an abutment sleeve for skin penetration. The complete structure can either be in one piece or the skin penetrating abutment could be connected to the fixture prior, during or after the implantation procedure by means of a screw connection or the like.

Figure 1:
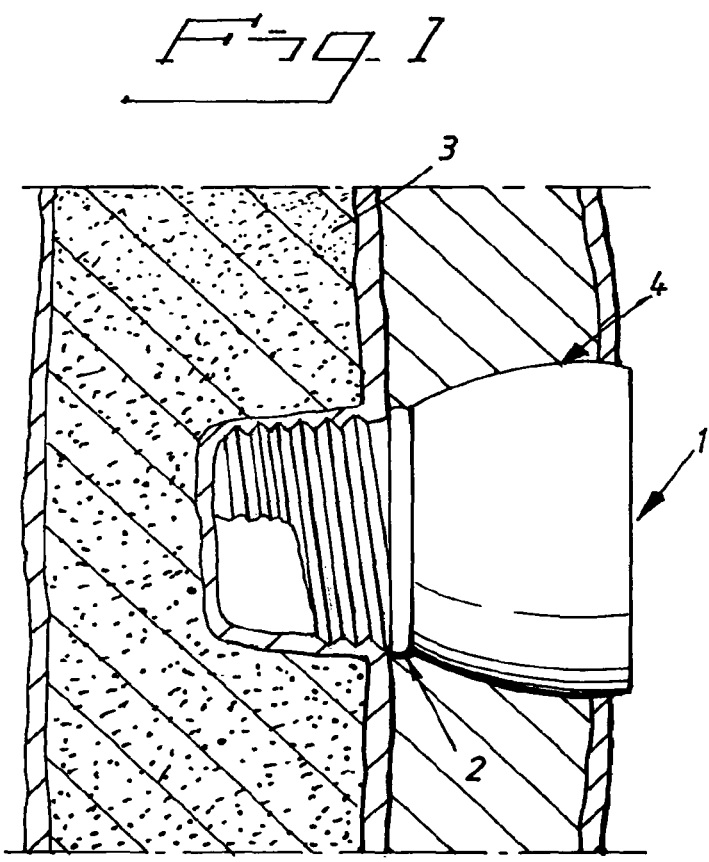
FIG. 1 illustrates an implant according to one embodiment of the present invention anchored in the bone in the craniofacial region of a person.

FIG. 1 illustrates a percutaneous implant 1 in accordance with embodiments of the present invention anchored in the bone in the craniofacial region of a person. The implant is may be used for a bone anchored hearing aid or the like. The implant comprises a screw-shaped bone anchoring element (fixture) 2 for permanent anchorage in the bone tissue 3 and an abutment device 4 for skin 5 penetration. The complete structure can either be in one piece or the skin penetrating abutment 4 could be connected to the fixture prior, during or after the implantation procedure by means of a screw connection or the like. The screw-shaped anchoring element, the so-called fixture 2 is made of titanium which has a known ability to integrate with the surrounding bone tissue, so-called osseointegration. The fixture has a threaded part 2a which is intended to be installed into the skull bone and a flange 2b which functions as a stop when the fixture is installed into the skull bone. The apical part of the fixture has a known tapping ability with in this case three self-tapping edges 2c. A fixture of this type is described in the above-mentioned SE 0002627-8 and will therefore not be described in any detail here.

The skin penetrating part, the abutment 4 of the implant, comprises a substantially conical abutment sleeve. Conical abutment sleeves are previously known per se as separate components or as an integral part with the fixture, a one-piece implant. The abutment sleeve is provided with a first coupling part in order to cooperate with a second coupling part (not shown) by means of snap-in action or the like.

According to embodiments of the present invention the shear modulus of the skin contacting part of the percutaneous implant abutment 4 has been reduced. Preferably the shear modulus should be less than approximately 35 GPa.

Figure 2:
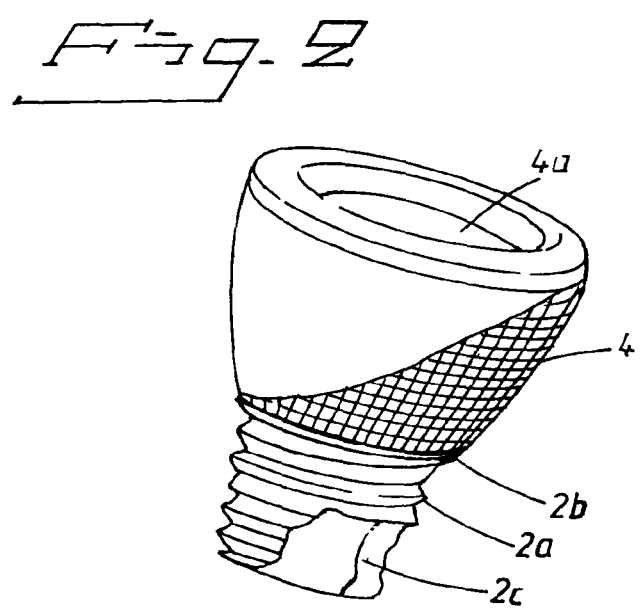
FIG. 2 illustrates an implant according to embodiments of the present invention for bone anchorage.

Specifically, the shear modulus is reduced by a modification of the surface of the skin contacting part of the percutaneous implant abutment, illustrated by the structured abutment surface in FIG. 2. According to a preferred embodiment the surface of the skin contacting part of the percutaneous implant abutment is coated with a biocompatible polymer or a ceramic material with a thickness of approximately 0.001 µm to approximately-50 µm. The coating is applied in such a way that non-interconnected pores or crevices are created. Generally the coating should be applied in such a way that a structured surface such as a porous surface or a surface with indentations or a fibrous surface is obtained. A typical porous surface is illustrated by the SEM picture in FIG. 4.

The polymer coating is comparatively soft and decreases the shear stresses on the skin. In certain embodiments, a layer of a porous polymer is used for the coating with a thickness of about 30 nm. Such design is allowing the skin to heal into the polymer matrix.

Also a polymer containing a pharmaceutical drug that increases the production of extra-cellular matrix proteins in the soft tissue, such as collagen or keratin, might be used. The increased stability of the tissue increases the resistance to shear stress.

Also other types of materials might be used for increasing the skin tissue integration. Specifically, chemical substances such as pharmaceutical drugs and antioxidants, or biochemical substances such as proteins, biopolymers, growth factors, DNA, RNA or biominerals might be used. These substances are then associated to the implant with a purpose of increasing the amount of, or number of connections to extra cellular matrix proteins. Antibiotic, steroid or anti-inflammatory substances might also be used.

As an alternative to said coatings or substances, or in combination, a surface enlargement treatment can be provided to the surface of the skin contacting part of the percutaneous implant in order to increase the surface roughness. Such treatment can be achieved by using techniques that includes grit-blasting, polishing, micro-machining, laser treatment, turning, anodic oxidation, oxidation, chemical etching, sintering or plasma deposition of a titanium surface. Preferably such treatment should result in a 10% surface increase, compared to a conventional machined surface and a roughness value Sa of approximately 0.5 µm to approximately-10 µm, measured by means of White Light Interferometry.

Figure 3:
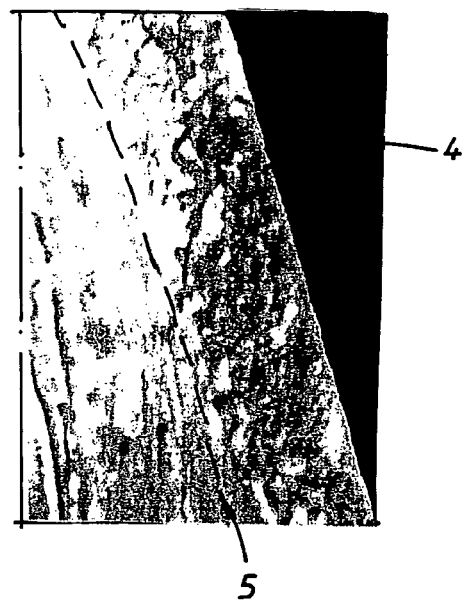
FIG. 3 is a LM picture of the interface between the skin and the contacting part of the implant abutment.

FIG. 3 is a LM picture of the interface between the skin 5 and the contacting part of the implant abutment 4 of a polyurethane coated titanium material. The figure illustrates the situation after a healing period of 8 days and indicates a substantial integration of the abutment into the skin 5.

Figure 4:
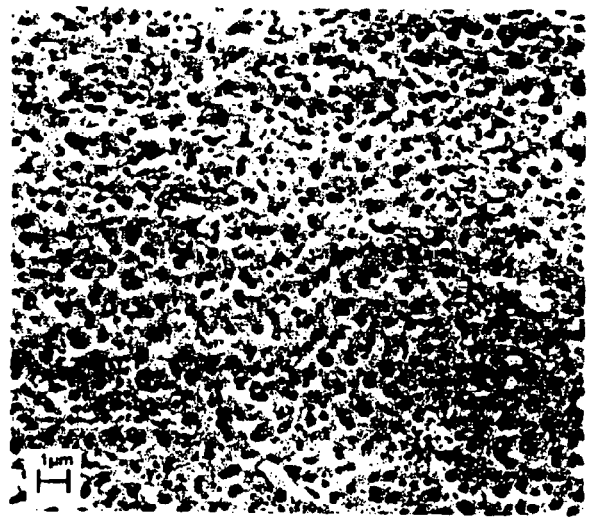
FIG. 4 is a SEM picture of the surface structure of the skin contacting part of the implant abutment.

FIG. 4 is a SEM picture of the surface structure of the skin contacting part of the implant abutment having an anodically oxidized surface.

It should be understood that only that part of the abutment surface which is in contact with the skin need to be modified. Other parts of the abutment such as the lower and upper end surfaces, i.e. the surfaces connected to the fixture and the coupling device respectively, might have a conventional, machined and/or polished surface.

According to one embodiment of the present invention, the surface of the skin contacting part of the percutaneously implant abutment is coated with a biocompatible polymer with a thickness of approximately 0.001 µm-to approximately 50 µm. According to a another embodiment, the surface of the skin contacting part of the percutaneously implant abutment is coated with a ceramic material with a thickness of 0.001 µm-to approximately 50 µm.

According to another embodiment, a surface enlargement treatment has been provided to the surface of the skin contacting part of the percutaneously implant abutment. Preferably a 10% surface increase, compared to a conventional machined surface, is created resulting in a roughness value Sa of 0.5 µm-to approximately 10 µm.

It should be understood that there are percutaneous implant as such that are made of polymers (catheters etc) but they are not bone anchored and they are not exposed to the typical shear forces that are the case for implants with inherent movements such as bone anchored hearing implants due to the generation of vibratory movements.

An advantage of embodiments of the present invention is to provide an implant abutment in which the shear forces between the implant abutment and the skin have been reduced. This improves wound healing and integration around bone anchored percutaneous implants.

According to another feature of embodiments of the present invention, the shear modulus of the skin contacting part of the percutaneously implant abutment is reduced. Preferably the shear modulus should be less than approximately 35 GPa.

In certain embodiments, the implant design includes a flange or a skirt perpendicular to the abutment orientation in order to mechanically increase the surface area and stability and thereby also reduce the shear stress on the implant-skin interface. Also the implant design might include one or more retention grooves or waists. Otherwise, however, the abutment should be designed without any sharp edges or corners in order to simplify the surface modification procedure.

Further features and advantages of the present invention are described in commonly owned and co-pending U.S. Utility patent application entitled "VIBRATOR FOR BONE CONDUCTING HEARING DEVICES," filed Nov. 24, 2009, which is a national stage application of PCT Application No. PCT/SE2008/000336, filed May 21, 2008; and commonly owned and co-pending U.S. Utility patent application entitled "ANCHORING ELEMENT" which is a national stage application under 35 USC §371 (c) of PCT Application No. PCT/SE2008/000338, filed on May 21, 2008. The content of these applications are hereby incorporated by reference herein.

It will be appreciated by persons skilled in the art that numerous variations and/or modifications may be made to the invention as shown in the specific embodiments without departing from the spirit or scope of the invention as broadly described. Specifically it should be understood that any combinations of the said surface modifications could be used, e.g. using composites, structured ceramic coatings, polymer/pharmaceutical drug coatings, anodized flange etc. The present embodiments are, therefore, to be considered in all respects as illustrative and not restrictive.

What is claimed is:

1. A percutaneous implant for a bone anchored implant device adapted to be anchored to a bone of a recipient, comprising:
   an abutment, including:
      a skin penetration body having a skin contacting surface; and
      a biocompatible coating disposed on the skin contacting surface, wherein
   at least one of:
   (i) the biocompatible coating comprises a biocompatible polymer having a thickness of equal to or greater than approximately 0.001 micrometers;
   (ii) the biocompatible coating has a composition such that the coated skin contacting surface has a shear modulus that is less than approximately 35 GPa;
   (iii) the percutaneous implant further comprises a bone anchor comprising a threaded exterior surface, wherein the threaded exterior surface has a maximum outer diameter that is less than a minimum outer diameter of the abutment; or
   (iv) the coating has a roughness value Sa of approximately 0.5 μm-10 μm.

2. The percutaneous implant of claim 1, wherein the biocompatible coating includes the thickness of equal to or greater than approximately 0.001 micrometers.

3. The percutaneous implant of claim 2, wherein the biocompatible coating comprises a biocompatible polymer having the thickness of equal to or greater than approximately 0.001 micrometers.

4. The percutaneous implant of claim 2, wherein the biocompatible coating comprises a ceramic material having the thickness of equal to or greater than approximately 0.001 micrometers.

5. The percutaneous implant of claim 1, wherein the biocompatible coating has a composition such that the coated skin contacting surface has the shear modulus that is less than approximately 35 GPa.

6. The percutaneous implant of claim 1, further comprising:
   the bone anchor comprising the threaded exterior surface, wherein the threaded exterior surface has the maximum outer diameter that is less than the minimum outer diameter of the abutment.

7. The implant according to claim 1 wherein the coating has the roughness value Sa of approximately 0.5 μm-10 μm.

8. A percutaneous abutment for a bone anchored implant device adapted to be anchored to a bone of a recipient, comprising:
   a skin penetration body having a skin contacting surface, wherein the abutment is configured such that the skin contacting surface is configured to integrate with recipient skin overlying the bone of the recipient,
   wherein at least one of:
   (i) the skin contacting surface includes at least one of non-interconnected pores or crevices configured to integrate with recipient skin overlying the bone of the recipient;
   (ii) the skin contacting surface includes at least one of porous surface features, indentations or fibrous surface features configured to integrate with recipient skin overlying the bone of the recipient;
   (iii) the skin contacting surface is coated with a polymer matrix configured such that skin overlying the bone of the recipient heals into the polymer matrix;
   (iv) the abutment is coated with a polymer; or
   (v) the skin penetration body is provided with a first coupling part configured to couple with another component that attaches to the percutaneous abutment via a snap-in action.

9. The percutaneous abutment of claim 8, wherein:
the skin contacting surface includes at least one of non-interconnected pores or crevices configured to integrate with recipient skin overlying the bone of the recipient.

10. The percutaneous abutment of claim 8, wherein:
the skin contacting surface includes at least one of porous surface features, indentations or fibrous surface features configured to integrate with recipient skin overlying the bone of the recipient.

11. The percutaneous abutment of claim 8, wherein:
the skin contacting surface is coated with the polymer matrix configured such that skin overlying the bone of the recipient heals into the polymer matrix.

12. The percutaneous abutment of claim 8, wherein:
the skin contacting surface is coated with a biocompatible coating on the skin contacting surface.

13. The percutaneous abutment of claim 8 wherein:
the abutment includes a coating configured to integrate with the recipient skin, and wherein the coating is comparatively soft and porous and has a thickness of approximately 30 nm.

14. The percutaneous abutment of claim 8 wherein:
the abutment is configured to increase production of extra-cellular matrix proteins in soft tissue of the recipient skin, thereby integrating the abutment with the recipient skin overlying the bone of the recipient.

15. The percutaneous abutment of claim 8 wherein:
the abutment is configured to increase at least one of the amount or number of connections to extra-cellular matrix proteins of the recipient skin, thereby integrating the abutment with the recipient skin overlying the bone of the recipient.

16. A percutaneous implant for a bone anchored implant device adapted to be anchored to a bone of a recipient, comprising:
an abutment, including:
a skin penetration body having a skin contacting surface of a modified configuration, wherein
at least one of:
(i) the implant is implanted in a recipient such that it is fixed to bone of the recipient; and
the modified surface has reduced shear forces between the abutment and skin of the recipient relative to that which would be the case in the absence of the modified surface; or
(ii) the modified configuration is a surface roughness having a value Sa of 0.5-10 micrometers.

17. The percutaneous abutment of claim 16, wherein:
the abutment is made of at least two different materials, at least one of the materials of the at least two different materials establishing the surface of the modified configuration.

18. The implant of claim 16, wherein:
the implant is implanted in a recipient such that it is fixed to bone of the recipient, and wherein the abutment is integrated with skin of the recipient.

19. The implant of claim 16, wherein:
the implant is implanted in a recipient such that it is fixed to bone of the recipient; and
the modified surface has prevented a dissociation between skin and the abutment and the encapsulation of the abutment in fibrous tissue.

20. The implant of claim 16, wherein:
the implant is implanted in the recipient such that it is fixed to bone of the recipient; and
the modified surface has reduced shear forces between the abutment and skin of the recipient relative to that which would be the case in the absence of the modified surface.

21. The implant device of claim 16, wherein:
the modified configuration is that resulting from a surface enlargement treatment.

22. The implant device of claim 16, wherein:
the modified configuration is the surface roughness having the value Sa of 0.5-10 micrometers.

23. The implant device of claim 16, wherein:
the implant is implanted in a recipient such that it is fixed to bone of the recipient; and
skin of the recipient overlying the bone of the recipient is healed into the surface of a modified configuration.

24. The percutaneous implant of claim 3, further comprising a ceramic material having a thickness of equal to or greater than approximately 0.001 micrometers, wherein the ceramic material corresponds to a second biocompatible coating.

25. The percutaneous abutment of claim 11, wherein:
the abutment is further coated with a ceramic material having a thickness of equal to or greater than approximately 0.001 micrometers.

26. The percutaneous implant of claim 1, wherein the biocompatible coating comprises the biocompatible polymer.

27. A percutaneous implant for a bone anchored implant device adapted to be anchored to a bone of a recipient, comprising:
an abutment, including:
a skin penetration body having a skin contacting surface; and
a biocompatible coating disposed on the skin contacting surface,
wherein at least one of:
(i) the implant includes a threaded section and an unthreaded section, wherein the unthreaded section extends longer than the threaded section in a longitudinal direction of the implant;
(ii) the implant further comprises a bone anchor comprising a threaded exterior surface, wherein the abutment and the bone anchor are separate components fastened together by a screw connection; or
(iii) the implant further comprises a bone anchor comprising a threaded exterior surface having a self-tapping configuration, wherein the bone anchor has a flanged section that functions as a stop to prevent further insertion into bone.

28. The percutaneous implant of claim 1, wherein the implant is implanted in a recipient, wherein skin abuts the abutment, and wherein the skin extends away from the abutment in at least two opposite directions for a distance that is at least a distance about equal to a radius of the maximum outer diameter of the abutment.

29. The percutaneous implant of claim 1, wherein the implant is implanted in a recipient such that the implant is anchored into bone and the abutment extends through skin of the recipient to a location above the skin of the recipient.

30. The percutaneous implant of claim 27, further comprising:
the bone anchor comprising the threaded exterior surface, wherein the abutment and the bone anchor are separate components fastened together by the screw connection.

31. The percutaneous implant of claim 27, further comprising:
the bone anchor comprising the threaded exterior surface having the self-tapping configuration, wherein the bone anchor has the flanged section that functions as the stop to prevent further insertion into bone.

32. The percutaneous abutment of claim 8, wherein the skin penetration body is provided with the first coupling part configured to couple with the another component that attaches to the percutaneous abutment via the snap-in action.

33. The implant of claim 1, wherein:
the implant includes the threaded section and the unthreaded section, wherein the unthreaded section extends longer than the threaded section in the longitudinal direction of the implant.

34. The percutaneous abutment of claim 27, wherein the skin penetration body is provided with a first coupling part configured to couple with another component that attaches to the percutaneous abutment via a snap-in action.

35. The percutaneous abutment of claim 1, wherein the skin penetration body is provided with a first coupling part configured to couple with another component that attaches to the percutaneous abutment via a snap-in action.

36. The percutaneous abutment of claim 16, wherein the skin penetration body is provided with a first coupling part configured to couple with another component that attaches to the percutaneous abutment via a snap-in action.

* * * * *